(12) United States Patent
Dawes et al.

(10) Patent No.: US 9,981,263 B2
(45) Date of Patent: May 29, 2018

(54) FLOW CONTROL APPARATUS FOR SAMPLE FLUIDS

(71) Applicant: EPREP PTY LTD, Ringwood, Victoria (AU)

(72) Inventors: Ernest Frederick Dawes, Ringwood (AU); Peter Alexander Dawes, Ringwood (AU); Reno Cerra, Ringwood (AU); Andrew Minett, Ringwood (AU)

(73) Assignee: EPREP PTY LTD, Ringwood, Victoria (AU)

( * ) Notice: Subject to any disclaimer, the term of this patent is extended or adjusted under 35 U.S.C. 154(b) by 142 days.

(21) Appl. No.: 14/758,443

(22) PCT Filed: Dec. 24, 2013

(86) PCT No.: PCT/AU2013/001526
§ 371 (c)(1),
(2) Date: Jun. 29, 2015

(87) PCT Pub. No.: WO2014/100859
PCT Pub. Date: Jul. 3, 2014

(65) Prior Publication Data
US 2015/0352543 A1    Dec. 10, 2015

(30) Foreign Application Priority Data

Dec. 31, 2012 (AU) ................. 2012905688
Jan. 30, 2013 (AU) ................. 2013900284
Nov. 20, 2013 (AU) ................. 2013904489

(51) Int. Cl.
*B01L 3/02* (2006.01)
*G01N 1/28* (2006.01)
(Continued)

(52) U.S. Cl.
CPC ........... *B01L 3/0217* (2013.01); *B01L 3/0275* (2013.01); *B01L 3/502* (2013.01); *F16K 5/08* (2013.01);
(Continued)

(58) Field of Classification Search
CPC .......... B01L 3/0275; B01L 3/502; F16K 5/08; F16K 15/02; G01N 1/14; G01N 1/28;
(Continued)

(56) References Cited

U.S. PATENT DOCUMENTS 5,770,029 A * 6/1998 Nelson ............. G01N 27/44791
204/453
6,613,525 B2   9/2003 Nelson et al.
(Continued)

FOREIGN PATENT DOCUMENTS

WO    1998039099 A2    9/1998
WO    2005121963 A2    12/2005
(Continued)

OTHER PUBLICATIONS

Written Opinion of the International Searching Authority dated Feb. 28, 2014 for corresponding International Application No. PCT/AU2013/001526, filed Dec. 24, 2013.
(Continued)

*Primary Examiner* — Jill A Warden
*Assistant Examiner* — Jacqueline Brazin
(74) *Attorney, Agent, or Firm* — David D. Brush; Westman, Champlin & Koehler, P.A.

(57) ABSTRACT

A flow control apparatus for facilitating treatment of a fluid containing a sample for analysis, includes: a body having spaced ends and defining a fluid flow passage arrangement that extends between the ends. The fluid flow passage arrangement includes two flow paths that are configured in parallel, merge within the body at least once, and respec-
(Continued)

tively contain a one-way check valve and a medium selected to treat or modify sample-containing fluid flowing therethrough.

17 Claims, 12 Drawing Sheets

(51) Int. Cl.
G01N 1/14 (2006.01)
F16K 5/08 (2006.01)
F16K 15/02 (2006.01)
G01N 30/08 (2006.01)
G01N 30/60 (2006.01)
G01N 1/40 (2006.01)
B01L 3/00 (2006.01)

(52) U.S. Cl.
CPC .............. *F16K 15/02* (2013.01); *G01N 1/14* (2013.01); *G01N 1/28* (2013.01); *G01N 1/405* (2013.01); *G01N 1/4077* (2013.01); *G01N 30/08* (2013.01); *G01N 30/6091* (2013.01); *B01L 2200/0631* (2013.01); *B01L 2200/0689* (2013.01); *B01L 2300/0681* (2013.01); *B01L 2400/0478* (2013.01); *B01L 2400/0487* (2013.01); *B01L 2400/0605* (2013.01); *G01N 2001/4088* (2013.01); *Y10T 137/7837* (2015.04)

(58) Field of Classification Search
CPC ...... G01N 1/405; G01N 1/4077; G01N 30/08; G01N 30/6091
USPC ........................................................ 422/541
See application file for complete search history.

(56) References Cited

U.S. PATENT DOCUMENTS

| 2004/0241874 A1* | 12/2004 | Abdel-Rehim | ....... B01L 3/0217 436/177 |
| 2010/0181517 A1* | 7/2010 | Paz Briz | ............... F15D 1/0015 251/324 |
| 2010/0240022 A1* | 9/2010 | McNeely | .......... B01L 3/502738 435/4 |

FOREIGN PATENT DOCUMENTS

WO  WO 2005/121963    * 12/2005
WO     2012158315 A1   11/2012

OTHER PUBLICATIONS

International Search Report dated Feb. 28, 2014 for corresponding International Patent Application PCT/AU2013/001526, filed Dec. 24, 2013.

* cited by examiner

FLOW CONTROL APPARATUS FOR SAMPLE FLUIDS

CROSS REFERENCE TO RELATED APPLICATIONS

The present application is based on and claims the benefit of: Australian provisional patent application Serial No. 2012905688, filed Dec. 31, 2012, the content of which is hereby incorporated by reference in its entirety; Australian provisional patent application Serial No. 2013900284, filed Jan. 30, 2013, the content of which is hereby incorporated by reference in its entirety; Australian provisional patent application Serial No. 2013904489, filed Nov. 20, 2013, the content of which is hereby incorporated by reference in its entirety;

The present application is a Section 371 National Stage Application of International Application No. PCT/AU2013/001526, filed Dec. 24, 2013, which is incorporated by reference in its entirety and published as WO 2014/100859 A1 on Jul. 3, 2014, in English.

FIELD OF THE INVENTION

This invention relates generally to the preparation of samples for analysis, and more particularly provides a flow control apparatus for facilitating treatment of a fluid containing a sample for analysis. The apparatus incorporates a one-way check valve and is especially useful in conjunction with a syringe and pipette.

BACKGROUND OF THE INVENTION

In analytical chemistry there are a range of sophisticated techniques available such as chromatography, mass spectrometry and other spectroscopy techniques but rarely can the sample be introduced directly into the instrument. Some modification of the sample is usually required, for example removal of interfering matrix, elimination of components that will interfere in the analysis, concentration of the sample, or switching the matrix or solution in which the sample components of interest are dissolved.

There are a variety of techniques involved in sample preparation but amongst the most common are filtering, targeted pre-separation to simplify the sample, concentration of the sample and changing the matrix. It has been reported that 40% of all analytical sample preparation requires Solid Phase Extraction (SPE) and 60% of all analytical sample preparation requires sample filtering during the procedure.

Syringes are used in many areas of laboratories including sample preparation for instrumental analysis. Fundamentally a syringe fulfils a triple role as a pump for displacing fluids, as a metering device for accurately determining the precise volume dispensed and the rate it is dispensed, and as a transport device. Syringes are used manually by hand or motor driven for automated operation.

Manual filtering generally involves aspirating the sample into the syringe, removing the syringe needle, fitting a filter membrane to the front of the syringe, dispensing the fluid through the filter, removing the filter and fitting a needle to the syringe for the next sample. Often this process leads to spillage and occupational health and safety issues related to repetitive strain injury. The process is slow when performed manually but is also not an efficient process to automate.

Syringe filters typically have high dead volume resulting in the need for considerable prefiltered sample to obtain the required quantity of filtered sample.

While there is a strong need for increased focus on laboratory automation or simplification of sample preparation processes using conventional syringe filters these processes are not easily amendable to automation.

Solid Phase Extraction (SPE) is based on partitioning molecules between a solid stationary phase and liquid mobile phase (e.g. liquid chromatography). The technique of SPE is most commonly practised by loading the sample on the top of the solid stationary phase bed and the flow through the bed is either driven by gravity or vacuum assisted, which means the pressure differential across the bed is limited to atmospheric pressure. Pressure differential limitation means large particle size separation media (usually 35-50 micron) must be used. Smaller particle sizes are not practical using normal SPE techniques as the fluid flow is too restricted for both drawing fluids through the bed and dispensing the fluids. Smaller particle seizes for the media would offer significant advantages in terms of increased absorption capacity of the media (From larger surface area per volume), improved extraction efficiencies, and the possibility for more selective separation of compounds from either other on the bed in the same way that smaller particle size gives greater compound separation efficiency on a liquid chromatography column.

Conventional SPE cartridges require a relatively large amount of solvent to elute the compounds from the SPE bed. Typically evaporation of this excess extraction solvent is then required as an additional part of the process.

The cartridges also do not lend the process to simple automation due to method process, connectability and manual manipulation issues during operation.

Elevated pressure driven SPE has been practised by using gas pressure above the SPE bed.

A further development of SPE for sample preparation was Micro Extraction by Packed Sorbent (MEPS) (described for example in US patent publication US2004/0241874) which is a syringe-based design. The stationary phase bed is packed into the barrel of a syringe. The syringe is then used to draw a defined volume of sample through the bed with bed and solvent conditions chosen to trap targeted compounds on the bed. Targeted compounds are then eluted off the bed by aspirating a suitable solvent through the bed. The targeted compounds are thereby desorbed into the solvent and thereby carried into the barrel of the syringe. The solution containing the targeted compounds is then dispensed from the barrel, back through the bed and into a vial for analysis, or directly into an analytical instrument.

The MEPS technique had large advantages over conventional SPE including ease of automation and reduced volumes of elution solvent containing the targeted compounds, which gives greater concentration of the eluted compounds for analysis. The disadvantage remains of having to use large particle size separation media because the sample must be aspirated through the media using suction from the syringe. Also, when the elution solvent is drawn through the MEPS bed, the sample compounds are spread evenly through the elution volume from the syringe barrel, meaning the concentration factor of the sample in the eluted solvent is not as high as could be achieved.

The sample needs to be drawn through the bed where targeted compounds are trapped and non-trapped material is dispensed to waste back through the bed. The compounds are released from the bed when an elution solvent is aspirated through the sorbent bed bringing the elution solvent containing the targeted compounds into the barrel of the syringe. This solution is then dispensed through the bed out through the needle. It is significant that the compounds of interest are spread evenly through the dispensed volume so they are somewhat diluted over the entire elution volume rather than primarily in a concentrated band, which would give greater detection sensitivity.

The discussion thus far has focused on sample preparation techniques that employ syringes, but much of the discussion applies equally to the use of pipette tips, including disposable pipette tips.

It is an object of the invention to at least in part address or alleviate one or more of the difficulties mentioned above.

Reference to any prior art or background information in this specification is not, and should not be taken as, an acknowledgment or any form of suggestion that this prior art or background information forms part of the common general knowledge in Australia or any other jurisdiction; or that this prior art or background information could reasonably be expected to be ascertained, understood and regarded as relevant by a person skilled in the art.

SUMMARY OF THE INVENTION

The invention entails a concept of providing a one-way check valve and a treatment medium in parallel passages at the front part of a syringe or pipette.

The invention provides, in one aspect, flow control apparatus for facilitating treatment of a fluid containing a sample for analysis, comprising:
  a body having spaced ends, which body defines therein a fluid flow passage arrangement extending between said ends;
  wherein the fluid flow passage arrangement includes two flow paths that are configured in parallel, merge within said body at least once, and respectively contain a one-way check valve and a medium selected to treat or modify sample-containing fluid flowing therethrough.

In another aspect, the invention provides a syringe assembly for facilitating treatment of a fluid containing a sample for analysis, comprising:
  a syringe barrel and a complementary plunger;
  a fluid flow passage arrangement in communication with a chamber defined by the barrel and the plunger;
  wherein the fluid flow passage arrangement includes two flow paths that are configured in parallel, and respectively contain a one-way check valve and a medium selected to treat or modify sample-containing fluid flowing therethrough.

In an embodiment, the one-way check valve is arranged to substantially prevent flow along the flow path containing the valve to the merge with the other flow path.

In an embodiment, the flow paths open separately from one of said ends of said body from spaced ports.

Preferably, the one-way valve is a plug seal valve.

The plug seal valve may include an integral plug seal having respective axially adjacent portions of relatively larger and smaller cross-section, the latter defining a peripheral sealing surface that engages a complementary female surface, and the former defining a shoulder that biases the valve closed under pressure of the fluid.

In an embodiment, the medium has ends spaced along its respective passages and frits or sorbent terminations are provided at one of both of said ends.

In one application, the medium is a sorbent bed selected to trap target compounds from said fluid as it passes through the sorbent bed, for subsequent recovery from the bed by an elution solvent. The sorbent bed may be, for example, a solid stationary phase bed, for practising Solid Phase Extraction (SPE) or Micro Extraction by Packed Solvent (MEPS) of said target compounds.

More generally, the medium is selected from the group comprising filtering media, monoliths and immobilised biologically active materials.

In an embodiment, the flow control apparatus is mounted within a barrel of a syringe, wherein the merged passages form a single duct communicable with a needle of the syringe, and the flow paths open separately into the interior chamber of the barrel.

Alternatively, the flow control apparatus can be provided as a separate unit attachable on the front of a syringe.

In a further aspect the invention provides a one-way plug seal valve having a valve seat and a valve plug, where the valve plug comprises respective axially adjacent portions of relatively larger and smaller cross-section, the latter defining a peripheral sealing surface that engages the valve seat and the former defining a shoulder that biases the valve closed under pressure of the fluid.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

The invention will now be further described, by way of example only, with reference to the accompanying drawings, in which.

DESCRIPTION OF EMBODIMENTS OF THE INVENTION

Figure 1:
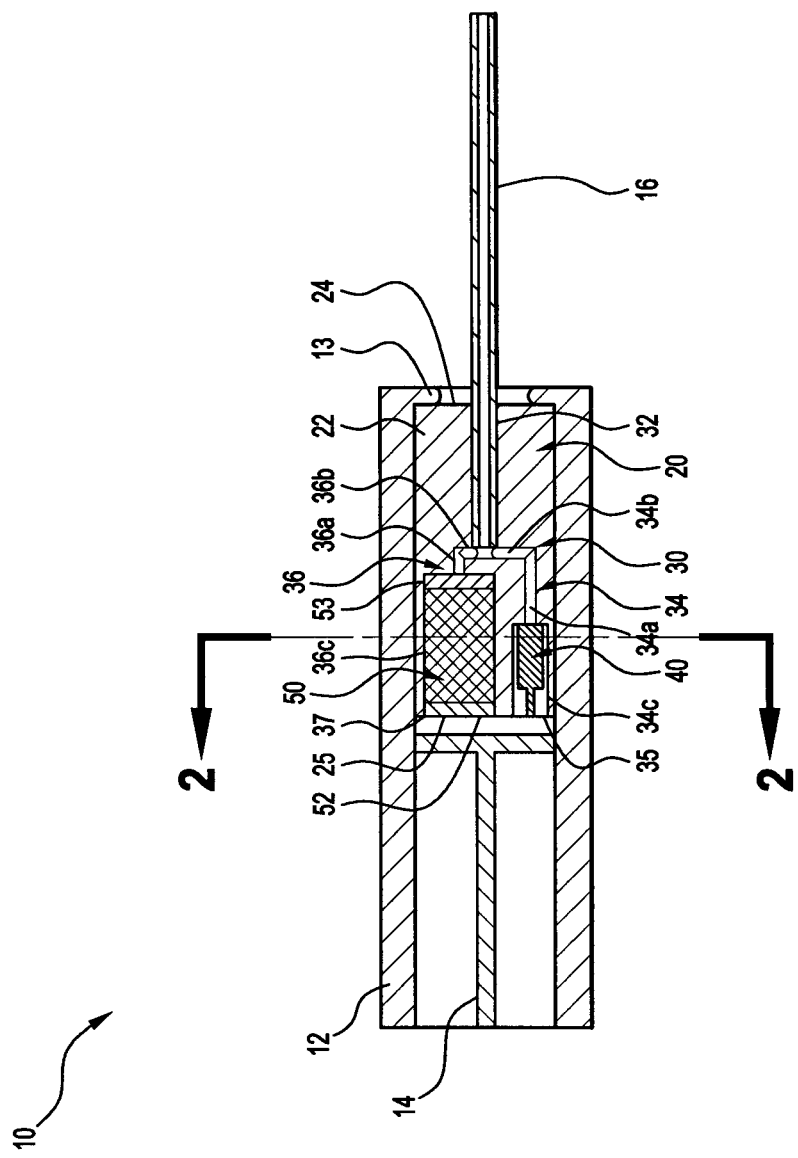
FIG. 1 is an axial cross-section of a flow control apparatus according to an embodiment of the invention, in the form of a check valve cartridge fitted in the end of a syringe barrel.
Figure 2:
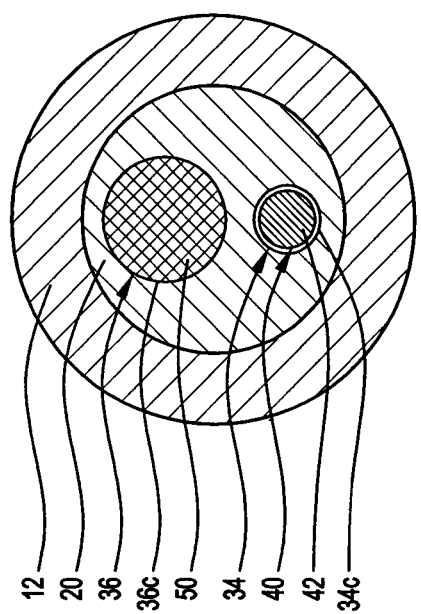
FIG. 2 is a cross-section on the line 2-2 in FIG. 1.

The syringe assembly 10 illustrated in FIGS. 1 and 2 includes a tubular syringe barrel 12 of annular cross-section, a reciprocable plunger 14, and a forwardly projecting hollow syringe needle 16. The front end of barrel 12 has a return lip 13 that locates a flow control apparatus in the form of a check valve cartridge 20. Cartridge 20 may be a press fit in the end of the barrel or otherwise secured in position, eg with adhesive.

Cartridge 20 comprises a generally cylindrical body 22 of a suitable inert material having spaced ends comprising end-faces 24,25. The body 22 is moulded or machined to define therein a fluid flow passage arrangement 30 extending between end-faces 24,25.

Passage arrangement 30 includes an axially extending bore 32 in body 22 of uniform diameter dimensioned to receive, in a press fit, syringe needle 16. This bore 32 opens at end-face 24, which abuts the return lip 13 of the front of syringe barrel 12. Passage arrangement 30 is completed by a pair of flow paths 34,36 in body 22 that are configured in parallel, merge within body 22 into the inner end of bore 32, and open separately at end-face 25 at respective ports 35,37. Flow paths 34,36 thereby communicate the interior of syringe needle 16 with the interior of syringe barrel 12 in a parallel flow arrangement.

Each flow path 34, 36 comprises a first duct portion 34a,36a extending parallel to the axis 11 of the syringe barrel and needle, a second duct portion 34b,36b extending radially to link portion 34a,36a to bore 32, and an enlarged chamber portion 34c,36c that respectively contains a one-way check valve 40 and a medium 50 selected to treat or modify fluid flowing through the medium.

Figure 3:
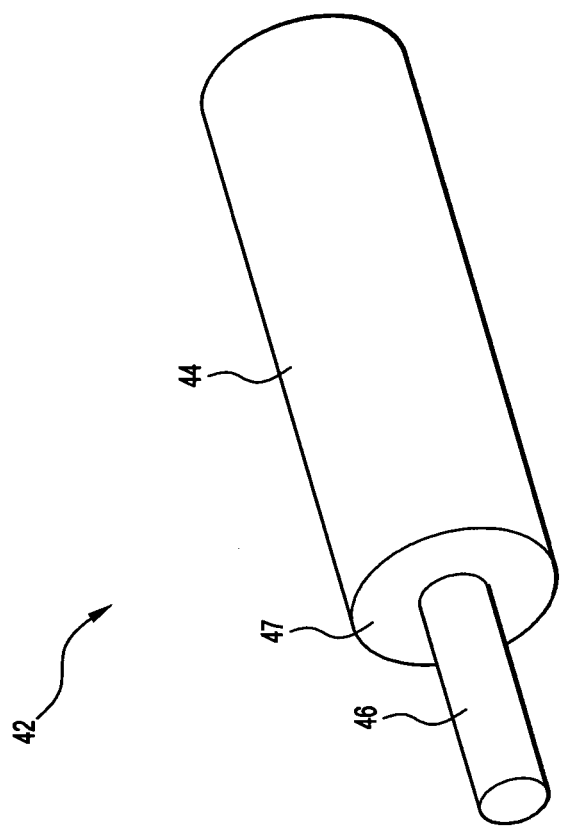
FIG. 3 is a three-dimensional view of the valve plug of the plug seal check valve in the embodiment of FIGS. 1 and 2.

In this embodiment, one-way check valve 40 is a plug seal valve including a valve plug 42 as shown in FIG. 3. Valve plug 42 is an integral moulding in a suitable rubber and consists of a first portion 44 of larger cross-section and a second portion 46 of smaller cross-section. In this case, plug portions 44,46 are solid coaxial cylinders. Larger plug portion 44 defines a cylindrical surface for seating and sealing the valve onto a cone sealing seat 45 at the junction between the chamber portion 36c and the axially parallel duct portion 36b of flow path 36. Smaller diameter portion 46 of the valve plug 42 provides a tail that defines a shoulder 47 by which the plug is biased closed onto the cone seat by fluid pressure.

It has been found that there are optimum dimensions for the diameter and length of the two cylindrical portions of the valve plug to obtain optimum operation. The larger diameter portion 44 effects pressure differential for sealing and aspiration back pressure. Its length ensures that the plug remains parallel in the valve during operation. The relative diameter of the smaller portion 46 determines 'spring) force' and its length will effect the normally closed position of the valve. The valve must allow opening (flow) at low differential pressures to ensure that sample is not drawn into the sorbent bed during aspiration. Conversely the valve ideally allows sealing during dispensing at very low flowrates (low differential pressure) to enable a wide range of applications Adopting a and c as the respective diameters of the smaller and larger portions 44,46,b as the overall length of the plug and d as the length of the larger diameter portion, the ratio c/a is conveniently in the range 2 to 4 while the ratio b/d is conveniently in the range 1.25 to 2.5. One example of an effective set of dimensions is c=1 mm, a=0.4 mm, b=4 mm and d=2.5 mm.

A suitable material for the plug 42 is a silicone rubber. Rubber hardness and constitution should be chosen to combine low flow rate sealing with chemical inertness so as not to interfere with, contaminate or absorb compounds from the sample fluid. A suitable material is a 40 duran hardness fluorosiloxane chosen for softness and chemical resistance.

The check valve depicted in FIGS. 1 to 3 has been found to perform reliably in flow rates ranging from 20 μL/min to 5 mL/min. Operation of the valve and flow paths were checked using dye solutions under a microscope. The plug seal valve also showed acceptable opening pressure, resulting in minimal back flow into the sorbent bed 50. The valve reliably closed immediately on liquid dispensing to ensure that substantially no sample was lost.

Medium 50 is typically a media bed that may comprise or contain but is not limited to SPE packing materials, SPE disks, sorbents, filtering media, monoliths and immobilised biologically active materials. Medium 50 is retained in chamber portion 36c of flow path 36 between frits or sorbent terminations 52,53, one of which is flush with the end face 25 of the valve cartridge body.

Figure 4:
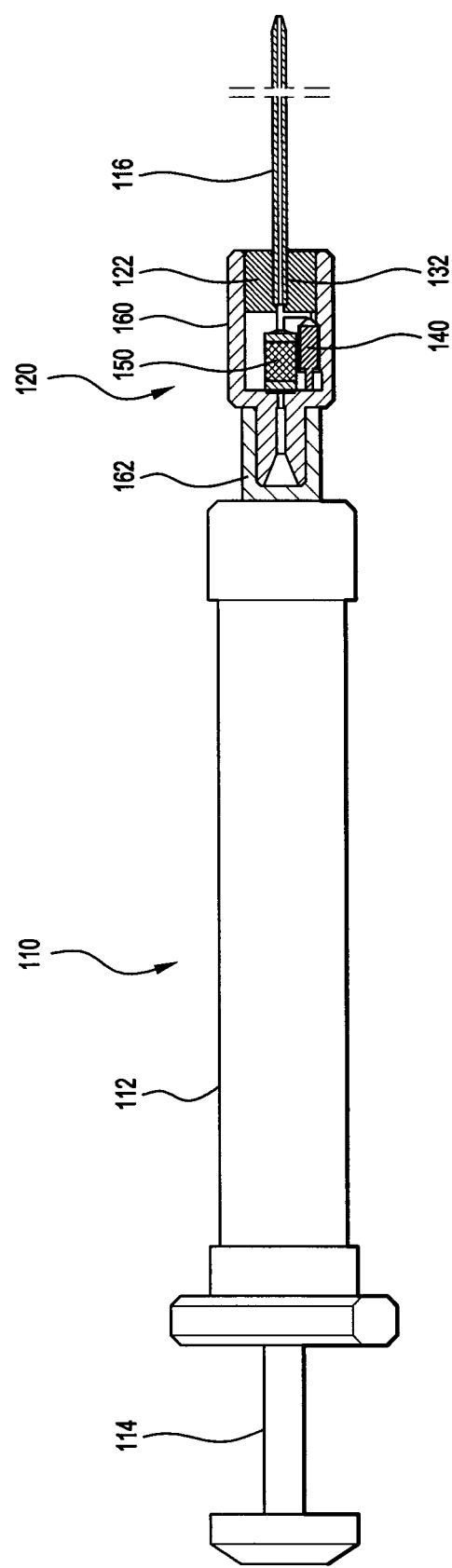
FIG. 4 is a partially sectioned alternative embodiment in which the check valve cartridge is a separate attachable unit for mounting on the front of a syringe.

It will be appreciated that check valve cartridge 20 can alternatively be provided as a separate self-contained unit 120 that can be attached on the front of a syringe, as illustrated in FIG. 4. In this arrangement, cartridge body 122 has a two-part body and is fitted within an outer housing 160 which is press fitted or screw threaded onto a syringe end fitting 162. Bore 132 can receive the syringe needle 116 as before, while housing 160 and fitting 162 include an axially located duct arrangement communicating flow paths 134, 136 with the interior of the syringe barrel. Additional radial grooves are provided in the end face 125 of body 122 to provide fluid communication between this duct arrangement and the flow paths 134, 136.

It will also be understood that the parallel flow paths, one-way check valve and treatment medium can be incorporated into a single piece plastic moulded, machined or 3D printed syringe barrel.

Figure 5:
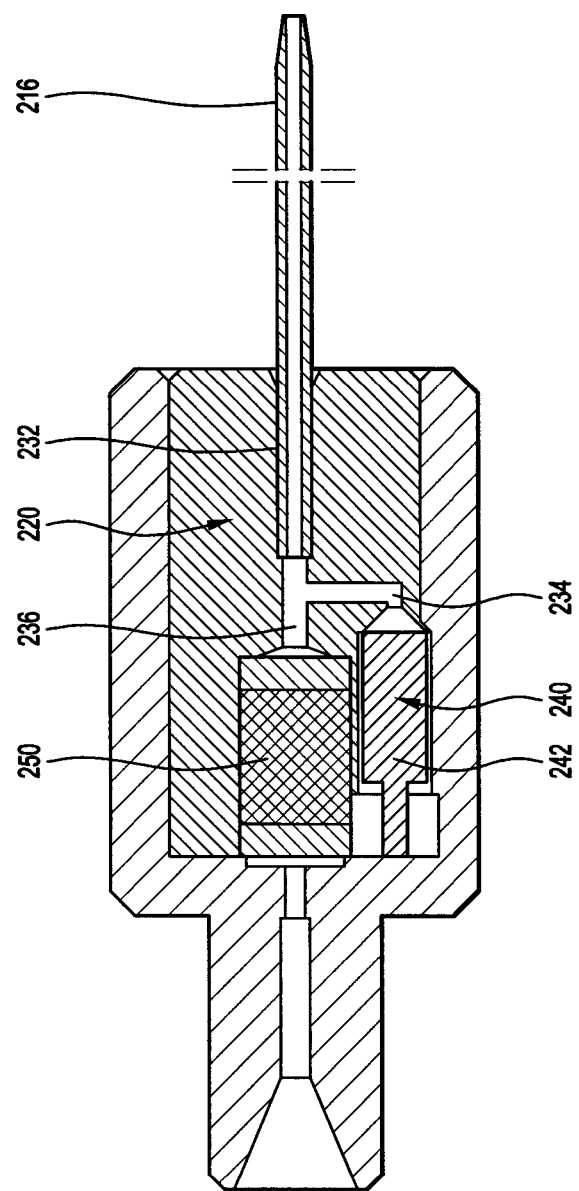
FIG. 5 is a further alternative embodiment with a different configuration of passages within the body of the check valve cartridge.

FIG. 5 illustrates a further embodiment in which body 220 is a single piece and flow path 234 is co-axially aligned with bore 232.

The particular operational advantage of the illustrated embodiment is that when the syringe plunger is retracted to aspirate fluid into the syringe through needle 16, the reduced pressure in the syringe opens valve 40, 140, 240, and there is then sufficient restriction to flow through the media bed 50 to substantially prevent any flow through the bed when the valve is open. On the other hand, once the fluid has been drawn into the syringe and the plunger of the syringe is depressed, the check valve defaults to its closed position, assisted by the pressure generated in the syringe barrel by the back pressure due to restriction of flow through the media bed. With the valve closed, the dispensed fluid will flow only through the bed to exit through the needle of the syringe.

Figure 6A:
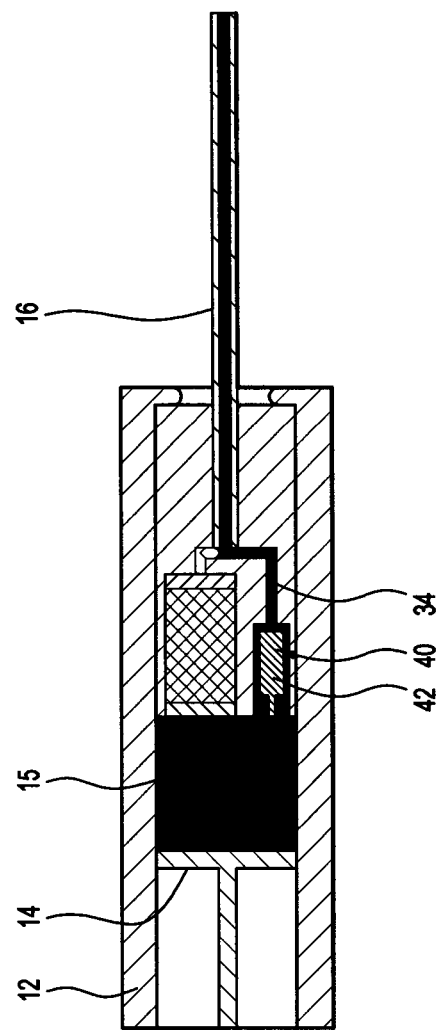
FIG. 6 depicts the four operational states (A to D) of the check valve cartridge of FIGS. 1 and 2 during the operation of a syringe for an SPE application.
Figure 6B:
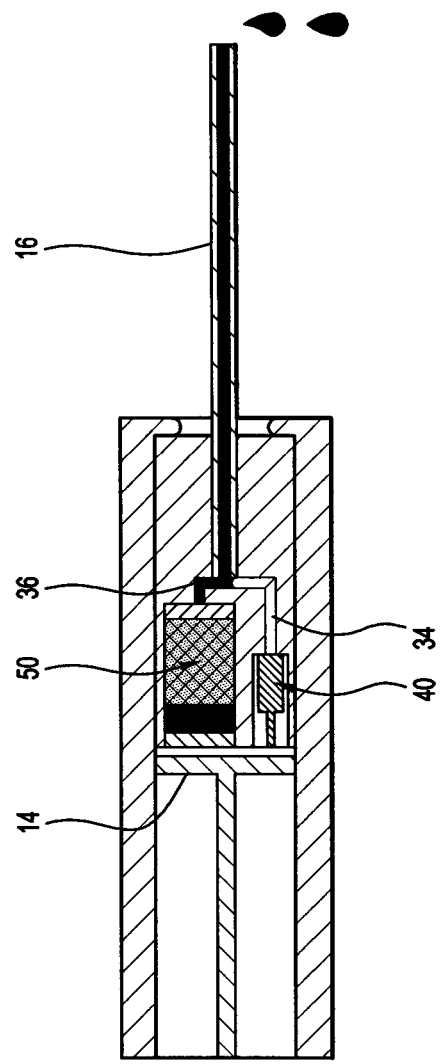
Figure 6C:
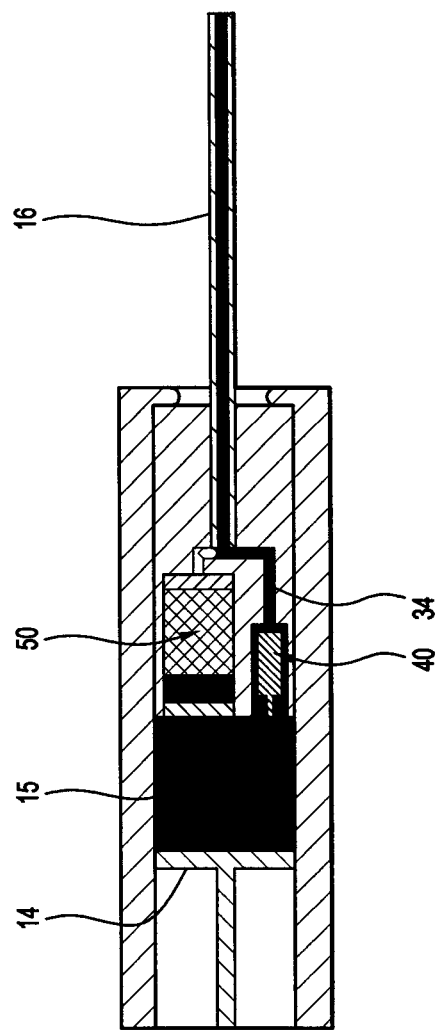
Figure 6D:
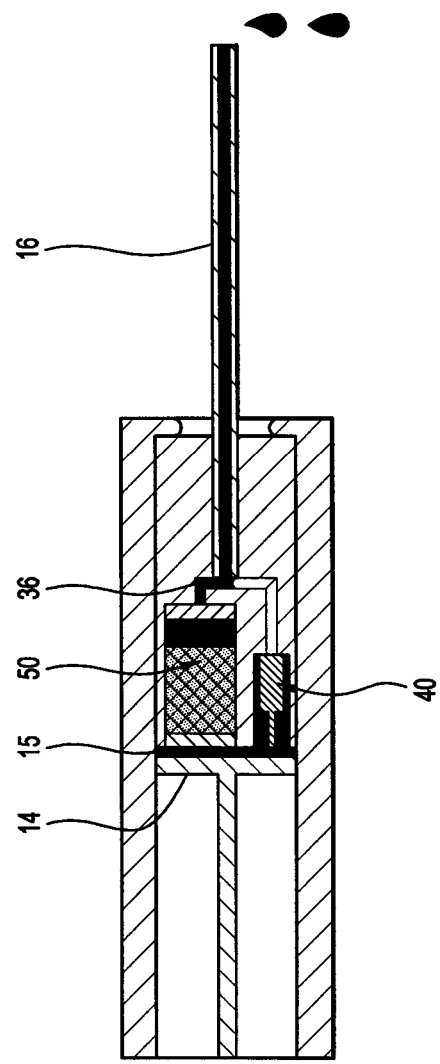

A typical operational flow sequence will now be described, with reference to FIGS. 6A to 6D, for an application where the media bed is an SPE medium chosen to trap targeted compounds from a sample liquid onto the bed. Drawback of the syringe plunger 14 opens the valve 40 and aspirates sample liquid into the barrel chamber 15 via flow path 34. The liquid does not pass through the medium or bed 50 (FIG. 6A). When the plunger 14 is depressed to close the valve, the sample is directed out through the sorbent bed 50, trapping targeted compounds on the bed (FIG. 6B). After brief contact with rinse fluid in the syringe needle, the syringe assembly is then moved to access an elution solvent. Here drawback of the syringe plunger 14 again opens the valve 40 and allows elution solvent to enter the barrel without traversing the sorbent bed (FIG. 6C). Finally, the plunger 14 is depressed to close the valve and solvent is directed through the sorbent bed 50, eluting the trapped compounds as it passes (FIG. 6D).

It will be appreciated that fraction collection and multiple solvent elution operations are also feasible.

Because the aspiration steps draw fluid through the check valve path and only the dispensing steps force fluid through the medium path, the reason for a minimum particle size restriction in media beds is removed. This permits the use of smaller particle sized media, for example down to as little as 1 micron diameter. The advantage of smaller media particle size is much higher compound capacity before saturation/breakthrough occurs and a much narrower band of eluted compound. The result is a nearly true chromatographic separation. The higher sample concentration in the elution band gives much greater sensitivity for analytical analysis.

Figure 7:
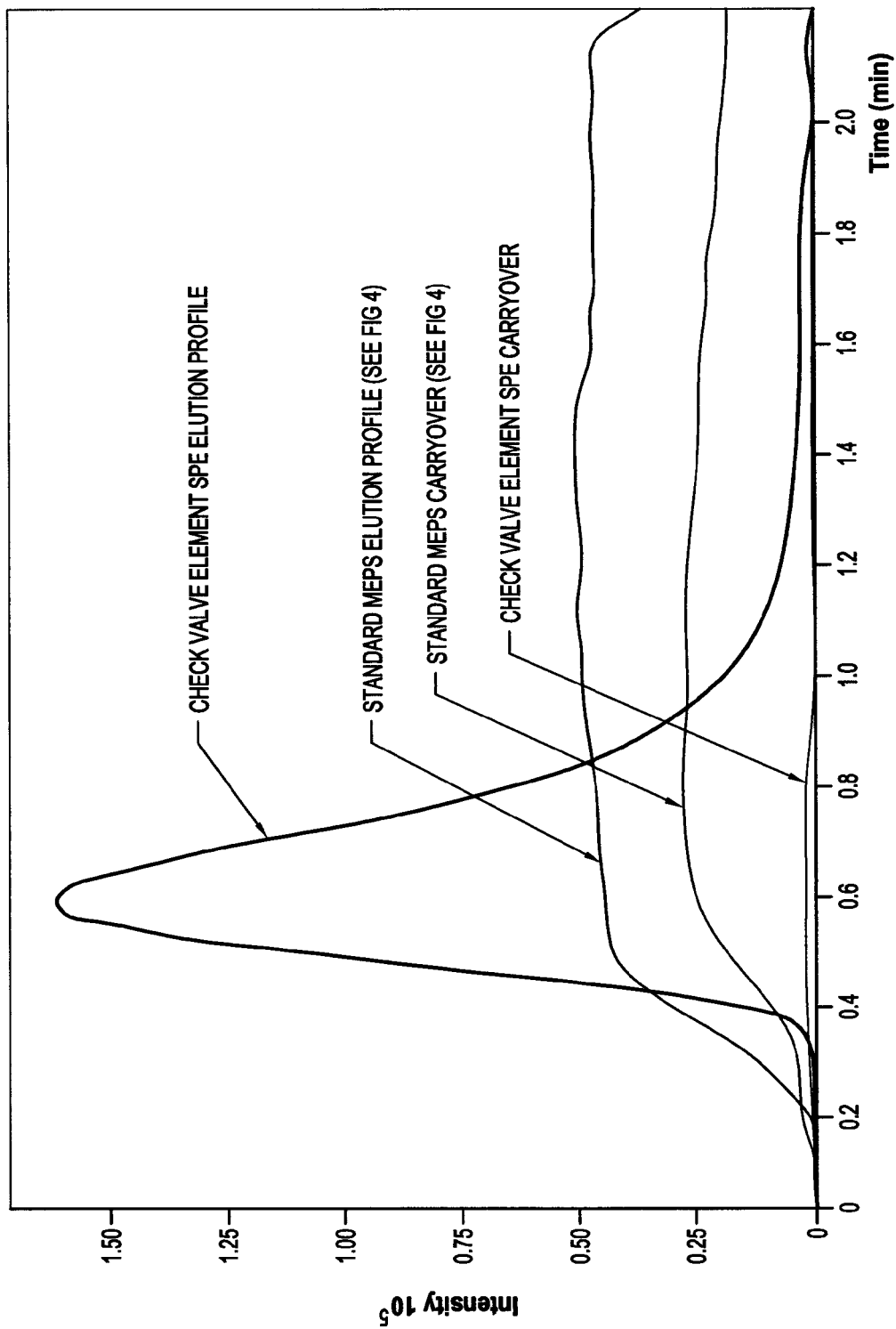
FIG. 7 is a graph illustrating the elution profile and carryover for a target compound in an SPE application, the graph also showing, for comparison purposes, a standard elution profile and carryover in a MEPS application.

These outcomes are illustrated in the graph of FIG. 7, which depicts an experimental SPE elution profile and SPE carryover for the embodiment of FIGS. 1 and 2 in comparison to the standard MEPS solution profile and MEPS carryover.

With the increased capacity and single directional flow of the sample through the bed the targeted compounds are focused in a narrow band at the top of the bed and when they are eluted with the elution solvent, the sample components can come off in a very narrow band or in a small volume. This small elution volume means the concentration of the targeted sample compounds can be very high, in fact higher than conventional SPE and even MEPS. This eliminates the need to concentrate the sample ready for analysis as is always necessary in conventional SPE.

For example, it has been demonstrated that 10 ml of sample can be processed down to 10 microliters of eluent containing the targeted compounds. This is a concentration factor of 1000:1 and can be achieved in minutes.

The flow characteristics of the device are such that there is minimal dead volume and good Gaussian elution profiles of the sample compounds can be achieved from the SPE cartridge.

The cleaning of a syringe, particularly in an automated system, is limited to filing and dispensing solvent multiple times. Conventionally, with each cycle of filling and dispensing, materials in the syringe flow path are diluted. With this check valve design, there is a one direction flow at all times through the areas of the syringe where contamination can occur, so the process is a purge of the syringe which is far more efficient cleaning process than repeated dilutions.

While originally designed for SPE applications, the ability to use small particle sorbent materials enables the check valve cartridge to be used as a pseudo liquid chromatography column where partition separation can be altered for various SPE media.

Combined with an automated system, the configuration of the invention can be programmed to elute and collect defined partition bands for concentration or targeted pre-analytical separation.

Often a liquid chromatography system is used as the sample preparation step for mass spectrometry involving specialised high pressure solvent delivery systems and valving systems. There are some sample analysis types where a syringe with a check valve cartridge as illustrated with SPE media can perform the same function as the sophisticated LC system.

Figure 8:
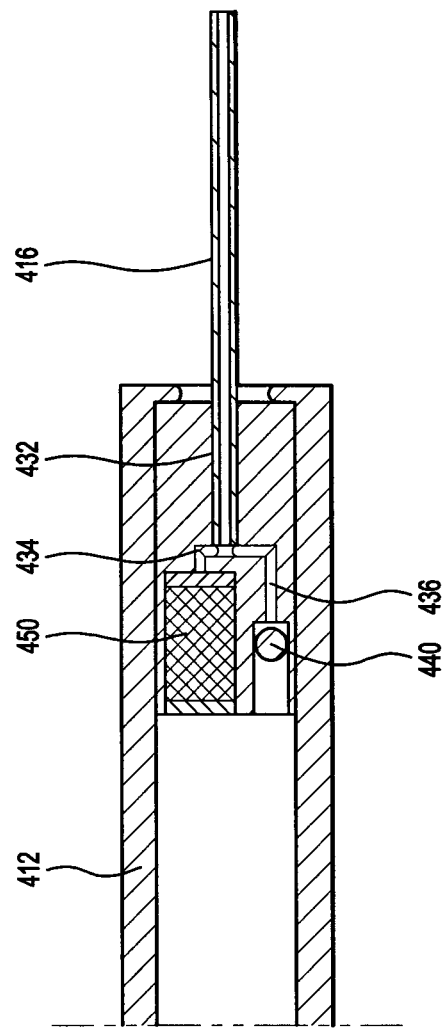
FIG. 8 is an axial cross-sectional view of a pipette tip incorporating a flow control apparatus similar to the embodiment of FIG. 1.

FIG. 8 illustrates a further embodiment generally similar to that of FIGS. 1 and 2, but with a ball valve 440 as the one-way check valve. Other possible forms of the check valve include, without limitation, flap valves, duck bill valves, and umbrella valves.

Figure 9:
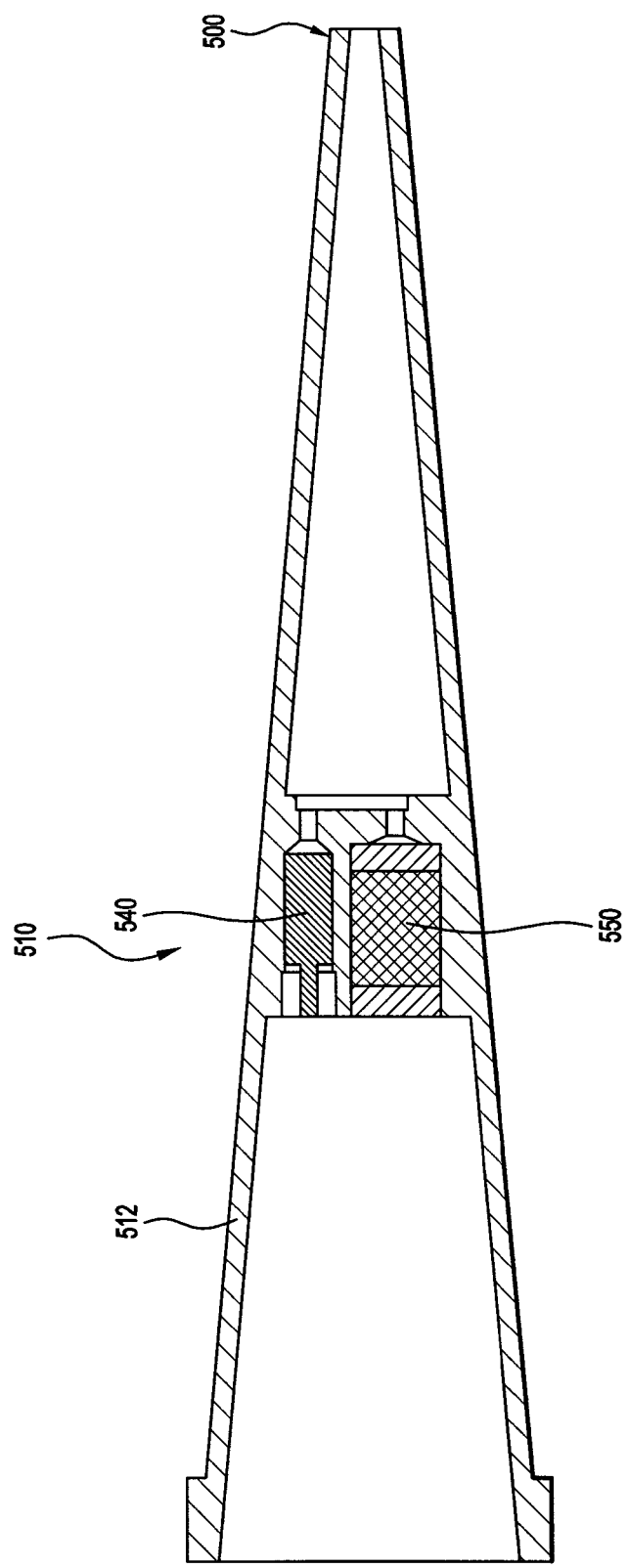
FIG. 9 is an axial cross-sectional view of a further embodiment in which the one-way valve is a ball valve.

FIG. 9 illustrates how the inventive concept is readily extendable to a disposal pipette 510 tip. Such tips can have a variety of volumes, materials and shapes, and can subsequently be used on a standard or modified pipettor. Again, after the fluid has been drawn into the barrel side 512 of the tip, the pipettor is depressed, the check valve 540 defaults to the closed position assisted by the pressure generated in the syringe component by the back pressure due to restriction of flow through the media bed 550. With the valve closed, the dispensed liquid from the pipettor tip can only flow through the media bed 550 and exit through the tip outlet 500.

The invention claimed is:
1. A flow control apparatus for facilitating treatment of a fluid containing a sample for analysis, comprising:
   a body having spaced ends, and the body defines therein a fluid flow passage arrangement extending between said ends;
   the fluid flow passage arrangement including two flow paths that are configured in parallel, and respectively contain a one-way check valve and a medium selected to treat or modify sample-containing fluid flowing therethrough, the medium having a fluid input side and a fluid output side, the one-way check valve having a fluid input side and a fluid output side, and the apparatus configured so as to substantially prevent fluid flow into the fluid output side of at least one of the medium and the one-way check valve,
   wherein the fluid flow passage arrangement is configured such that the two flow paths are merged to form a common flow path on the fluid input side of the one-way check valve and the fluid output side of the medium,
   and wherein the fluid flow passage arrangement is configured such that the two flow paths are merged to form a fluid reservoir on the fluid output side of the one-way check valve and the fluid input side of the medium,
   and wherein the fluid flow passage arrangement is configured such that:
   (i) upon aspiration of a fluid through the common flow path in a direction toward the two flow paths, the one-way check valve opens to allow the fluid to pass from the input side to the output side of the one-way check valve, and the fluid is substantially prevented from flowing through the medium, and
   (ii) upon ejection of a fluid from the fluid reservoir toward the common flow path, the one-way check valve closes, to allow the fluid to pass from the input side to the output side of the medium, and the fluid is substantially prevented from flowing through the one-way check valve.

2. The flow control apparatus according to claim 1, wherein said flow paths open separately from one of said ends of said body at spaced ports.

3. The flow control apparatus according to claim 1, wherein said one-way check valve is a plug seal valve.

4. The flow control apparatus according to claim 3, wherein said plug seal valve includes an integral seal plug having respective axially adjacent portions of relatively larger and smaller cross-section, the latter defining a peripheral sealing surface that engages a complementary female surface, and the former defining a shoulder that biases the one-way check valve closed under pressure of the fluid.

5. The flow control apparatus according to claim 4, wherein the portions of relatively larger and smaller cross-section are generally cylindrical and:
   (i) the ratio of the diameter of the portion of larger cross-section to the diameter of the portion of smaller cross-section is in the range 2 to 4, and
   (ii) the ratio of the combined length of both portions to the length of the portion of smaller cross-section is in the range 1.25 to 2.5.

6. The flow control apparatus according to claim 1, wherein said medium has ends spaced along its respective passage and frits or sorbent terminations are provided at one of both of said ends of the medium.

7. The flow control apparatus according to claim 1, wherein said medium is a sorbent bed selected to trap targeted compounds from said fluid as it passes through the sorbent bed, for subsequent recovery from the bed by an elution solvent.

8. The flow control apparatus according to claim 7, wherein the sorbent bed is a solid stationary phase bed, for practising Solid Phase Extraction (SPE) or Micro Extraction by Packed Solvent (MEPS) of the targeted compounds.

9. The flow control apparatus according to claim 1, wherein said medium is selected from the group comprising filtering media, monoliths and immobilised biologically active materials.

10. The flow control apparatus according to claim 1, mounted within a barrel of a syringe, wherein said merged paths form a single duct communicable with a needle for the syringe, and said flow paths open separately into the interior chamber of said barrel.

11. The flow control apparatus according to claim 1, provided as a separate unit attachable on the front of a syringe.

12. A syringe assembly for facilitating treatment of a fluid containing a sample for analysis, comprising:
    a syringe barrel and a complementary plunger; and
    a flow control apparatus in communication with a chamber defined by the barrel and the plunger, the flow control apparatus comprising:
    a body having spaced ends, and the body defines therein a fluid flow passage arrangement extending between said ends;
    the fluid flow passage arrangement including two flow paths that are configured in parallel, and respectively contain a one-way check valve and a medium selected to treat or modify sample-containing fluid flowing therethrough, the medium having a fluid input side and a fluid output side, the one-way check valve having a fluid input side and a fluid output side, and the apparatus configured so as to substantially prevent fluid flow into the fluid output side of at least one of the medium and the one-way check valve,
    wherein the fluid flow passage arrangement is configured such that the two flow paths are merged to form a common flow path on the fluid input side of the one-way check valve and the fluid output side of the medium,
    and wherein the fluid flow passage arrangement is configured such that the two flow paths are merged to form a fluid reservoir on the fluid output side of the one-way check valve and the fluid input side of the medium,
    and wherein the fluid flow passage arrangement is configured such that:
    (i) upon aspiration of a fluid through the common flow path in a direction toward the two flow paths, the one-way check valve opens to allow the fluid to pass from the input side to the output side of the one-way check valve, and the fluid is substantially prevented from flowing through the medium, and
    (ii) upon ejection of a fluid from the fluid reservoir toward the common flow path, the one-way check valve closes, to allow the fluid to pass from the input side to the output side of the medium, and the fluid is substantially prevented from flowing through the one-way check valve.

13. The syringe assembly according to claim 12, wherein said one-way check valve is arranged to substantially prevent flow along the flow path containing the one-way check valve.

14. The syringe assembly according to claim 12, wherein said flow paths open separately into said chamber.

15. The syringe assembly according to claim 12, wherein said one-way valve is a plug seal valve.

16. The syringe assembly according to claim 15, wherein said plug seal valve includes an integral seal plug having respective axially adjacent portions of relatively larger and smaller cross-section, the latter defining a peripheral sealing surface that engages a complementary female surface, and the former defining a shoulder that biases the one-way check valve closed under pressure of the fluid.

17. The syringe assembly according to claim 16, wherein the portions of relatively larger and smaller cross-section are generally cylindrical and:
    (i) the ratio of the diameter of the portion of larger cross-section to the diameter of the portion of smaller cross-section is in the range 2 to 4, and
    (ii) the ratio of the combined length of both portions to the length of the portion of smaller cross-section is in the range 1.25 to 2.5.

* * * * *